United States Patent [19]

Grendahl

[11] Patent Number: 4,503,570
[45] Date of Patent: Mar. 12, 1985

[54] INTRAOCULAR LENS

[76] Inventor: Dennis T. Grendahl, 150 Pennisula Rd., Medicine Lake, Minn. 55441

[21] Appl. No.: 398,322

[22] Filed: Jul. 15, 1982

[51] Int. Cl.³ ............................ A61F 1/16; A61F 1/24
[52] U.S. Cl. ............................................................ 3/13
[58] Field of Search ............................................ 3/13, 1

[56] References Cited

U.S. PATENT DOCUMENTS

| 3,979,780 | 9/1976 | Boniuk | 3/13 |
| 4,249,271 | 2/1981 | Poler | 3/13 |
| 4,403,354 | 9/1983 | Rainin | 3/13 |

OTHER PUBLICATIONS

"The Leiske Physioflex Style 10 Anterior Chamber Lens", Surgidev Advertisement Brochure, Surgidev Corp., 1421 State Street, Santa Barbara, California, Jan. 4, 1981.

Primary Examiner—Ronald L. Frinks
Attorney, Agent, or Firm—Hugh D. Jaeger

[57] ABSTRACT

Intraocular lens including a plano-convex lens and a plurality of flexible closed loops spaced about a circumference of an edge of the lens, one end of each closed loop fixedly secured into a hole in the edge and the other end of the closed loop in slidable engagement with an other hole in the edge, the other hole of a larger geometrical cross section than the cross section of the slidable end of the closed loop thereby providing an all-size lens. The arms of each loop can be planar or vaulted. A geometrical section of loop material such as a U-shaped curve or S-shaped curve can be positioned in the loop providing for additional sizing, adjusting and positioning of the slidable end of the loop. Pressure-relief ports can be provided through a port in the convex surface, the plano surface, or the edge or any combination thereof. Pressure relief can also be provided through an elliptical or notched hole for the slidable end of the loop, or a notched or tapered portion of the slidable end of the loop.

5 Claims, 9 Drawing Figures

INTRAOCULAR LENS

BACKGROUND OF THE INVENTION

1. Field of the Invention

The present invention relates to a surgical prosthesis and, more importantly, pertains to an implantable intraocular lens with a slidable loop thereby providing that the lens is accommodated by substantially all sizes of eyes.

2. Description of the Prior Art

The prior art intraocular lenses have been manufactured to a number of sizes denoted as diametrical lengths. These diametrical lengths generally range from 10.5 to 13.5 mm. Consequently, surgeons and hospitals are required to stock a supply of the most common size implantable lens along with other sizes for surgical procedures.

During surgery, it sometimes occurred that the first lens intended for implantation may not have been entirely accommodated by an individual's eye, requiring the surgeon to utilize the next smaller or next larger size. This then requires that the surgeon open and remove a second and sometimes even a third sterile lens for implantation, resulting in considerable time and motion expenditure, in addition to the expense of the other opened but unused lens.

The prior art has heretofore offered few types of all-size lens for implant in the eye. The lenses have usually been fixed in geometrical structure and relationship, and have been implanted based on the requirements of the individual's eye for 4-point fixation, usually in the anterior chamber.

Also, not all eyes are the same size, thereby requiring a size in between that of commonly manufactured lens. Further, the eye may exert pressure against the loops requiring that the sides of the loops adjust accordingly. Prior art lenses have never accommodated these two particular prior art points.

The present invention overcomes the disadvantages of the prior art by providing an all-size lens with a slidable loop on at least one of the two closed loops. The slidable loop also can include a pressure-relief system eliminating any pressure which may build up in the hole accommodating the sliding long end. The slidable loop is adjustable to the size of an eye as well as being flexible. The sliding loop is suitable for lenses which utilize four point fixation as well as lesser points of fixation such as three or less. The configuration offers relative ease of handling and positioning by the surgeon in the human eye.

SUMMARY OF THE INVENTION

The general purpose of the present invention is to provide an implantable intraocular lens which is accommodating to all sizes of eyes through a slidable loop. In addition, the slidable loops will provide required flexibility during movement and touch of the eye. The loops may also include a pressure-relief system to relieve any pressure which may build up in a hole of the sliding loop structure.

According to the present invention, there is provided a lens such as a plano-convex lens including a plano surface, a convex surface and an edge about the circumference having a finite height, a plurality of spaced holes for accepting closed loops, one of the holes of like or slightly larger diameter than the other and at last one closed loop, one end of the closed loop secured into a hole and the other end of the closed loop in slidable engagement with the other hole whereby the free end of the loop is slidable in and out of the hole thereby inherently adjusting the closed loop extending beyond the edge of the lens. A predetermined geometrical configuration such as an S-shaped or U-shaped curve can be positioned toward the base of the closed loop for accommodating and reducing the length of the movement going from a larger size to a smaller size.

According to another embodiment of the present invention, there is provided a pressure-relief system between the slidable and free end of the closed loop and the larger hole in the lens. This pressure-relief system operates on the principle of providing a path for fluid and internal air pressure to flow along the length of the slidable loop or out of the hole as required.

According to other embodiments of the present invention, there is provided a pressure-relief system which can include a port through the plano, convex or edge surfaces of the lens intersecting the end of the slidable hole; a difference in geometrical cross section between the slidable free end of the loop and the hole such as where the hole would have an elliptical cross section while the loop has a circular cross section; the loop would have a finite tapered free end while the hole would have a circular cross section; and, either the hole could have a longitudinal groove, notch, etc., or the free slidable end of the loop could have a groove, notch, etc. Of course, a larger hole for encompassing the slidable loop will pass any pressures which might occur during any possible flexing.

A significant aspect and feature of the present invention is an intraocular lens which can be positioned in the eye as an all-size lens in that the eye inherently provides the placement of non-reactionary forces to result in the slidable loops of the lens adjusting to the proper size.

Another aspect and feature of the present invention is an all-size lens which is particularly advantageous to the surgeon as well as the hospital in that the surgical supply only needs to stock the one or possibly two sizes of all-size lenses for implant in the eye.

A further significant aspect and feature of the present invention is a pressure-relief system inherently configured and structured into the slidable loop structure for relieving any pressures which may possibly build up during flexing.

An additional significant aspect and feature of the present invention is a geometrical section which provides for adjustability of a flexible loop about the circumference of the lens. The geometrical section provides for inherent size reduction or expansion of the loop between the interior of the eye and the edge of the lens. While the geometrical section is disclosed for a closed loop, the principles of the present invention are also applicable to any type of loop whether the loop be closed or open. The lens can be plano-convex, aspheric, convex plano, or the like for implant into the human eye.

Having thus described the invention, it is a principal object hereof to provide an all-size lens.

An object of the present invention is to provide an all-size lens which can be accommodated to any size eye. This is accomplished through a closed loop where one end of the loop is secured in a hole in the edge and the other end is in slidable engagement with a hole in the edge.

Another object of the present invention is to provide a geometrical section such as an S-shaped, U-shaped, or other like section in a portion of the loop providing for adjustability, expansion and compression of the loop conforming to the eye.

A further object of the present invention is to provide a pressure-relief system between a closed loop and the lens including a geoemtrical member or difference of geometrical members interacting, providing for relief of pressure, inherent or otherwise, existing in the hole where the free end of the closed loop is slidably engageable. Whatever pressure of fluids or gases which may exist is inherently dissipated through the geometrical relief member.

An additional object of the present invention is that when the eye compresses the sliding loop, the loop end goes farther into the optic offsetting the oil canning tendency which vaulted lenses undergo.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
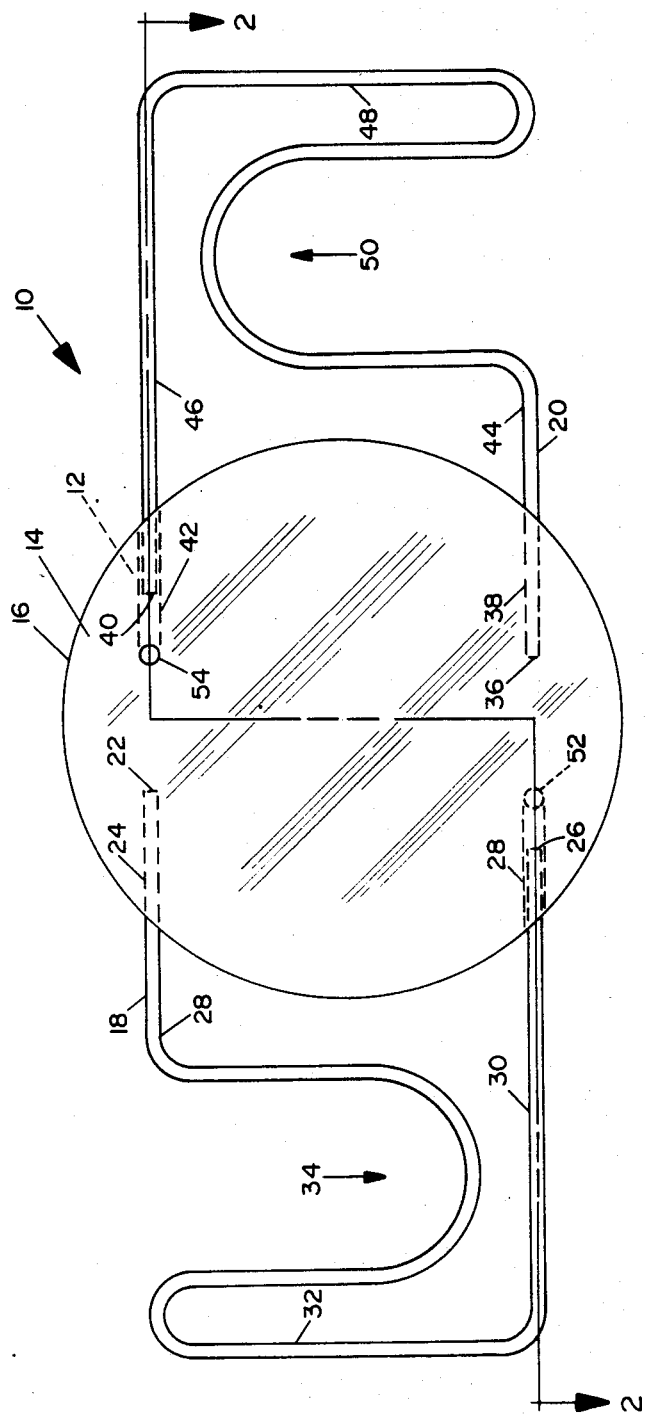
FIG. 1 illustrates a top view of an all-size lens, the present invention.
Figure 2:
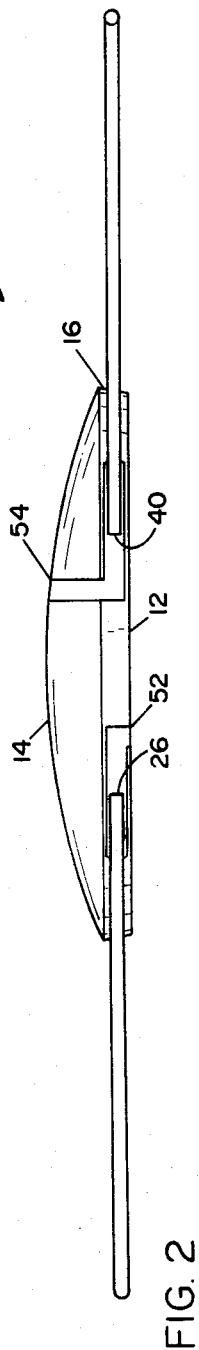
FIG. 2 illustrates a view taken along line 2—2 of FIG. 1.

FIG. 1 illustrates a top view of the present invention, an all-size intraocular lens 10. The all-size lens 10 includes a plano surface 12, as also illustrated in FIG. 2, a convex surface 14, and a finite edge surface 16 joining the plano surface 12 to the convex surface 14. The edge 16 has a finite height about the entire circumference. Two opposing closed-end, flexible, smooth, round loops 18 and 20 position and secured at edge 16 of the lens, as now described in detail for the loop 18, as loop 18 and 20 are exactly identical in geometry and structure in this example. The lens and loops can be made of polymethylmethacrylate ("PMMA") or like material.

End 22 of loop 18 secures into hole 24 which extends through the edge 16 and partially into and adjacent the plano surface 12. The end is secured into the lens by known processes. The other end 26 is in slidable engagement with a hole 28 extending into the lens and through the edge circumference 16. The circular cross section of hole 28 is slightly larger than the cross section of the end of the loop 26. The loop includes the two arm segments 28 and 30, a base 32, and a geometrical section 34. The geometrical section 34 is positioned to allow for flexibility and adjustability of the loop to a desired memory and size when finally implanted in the eye. In this particular example, for purposes of illustration only and not to be construed as limiting of the present invention, there is illustrated an integrated S curve which includes the base 32 and the geometrical portion 34. Describing the geometrical section as a unit, the section 34 assumes the shape of an elongated U, or an ovoid, a paraboloid, or semi-circle, such that there is an open portion and a geometrical space provided adjacent the secured end of the arm of the flexible loop by the geometrical adjusting section 34.

Loop 20 includes an end 36, hole 38, slidable end 40, and hole 42 of a slightly larger cross section than the cross section of slidable end 40, secured arm 44, slidable arm 46, base 48, and geometrical section 50 and is likewise identical to loop 18.

Pressure-relief ports 52 and 54 can be provided at the end of holes 28 and 42. In this particular example, the pressure-relief port 52 at the end of hole 28 extends downwardly through the plano surface 12 while pressure-relief port 54 at the end of hole 42 extends upwardly through the convex surface 14. Whether the pressure-relief ports extend downward or upward is a matter of medical and manufacturing consideration. The ports could extend through the plano surface, both ports could extend through the convex surface, or the ports could extend through the edge surface as illustrated in an alternative embodiment of FIG. 3, or in any combination thereof.

FIG. 2 illustrates a sectional view taken along line 2—2 of FIG. 1 where all numerals correspond to those elements previously described. Particular attention is drawn to the placement of the ports 52 and 54 through surfaces 12 and 14 respectively.

Figure 3:
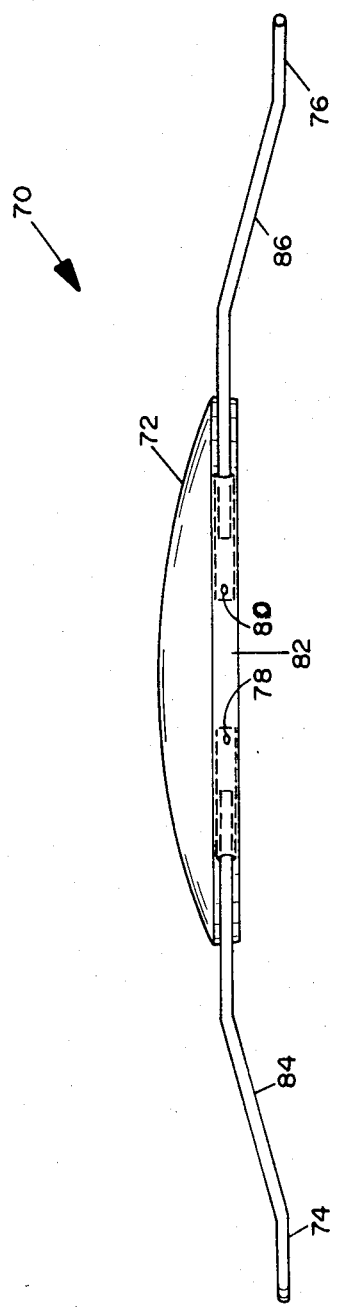
FIG. 3 illustrates a side view of the all-size lens, an alternative embodiment of the flexible loops.

FIG. 3 illustrates a side view of an alternative embodiment of an all-size intraocular lens 70. The lens and closed loop structure is identical to that of FIGS. 1 and 2, and additionally includes vaulted, also known as ramped, arms where the vault or ramp is positioned between the base of the loop and the edge of the lens. The lens 70 includes a plano-convex lens 72, and opposing flexible closed loops 74 and 76 as previously described in detail. One end of the loops is secured while the other end of the loops is in slidable engagement with the hole. All elements in the figure correspond to those of FIGS. 1 and 2. The only difference is that in this alternative embodiment, pressure-relief ports 78 and 80 are provided through the edge surface 82 of the lens. Ramps 84 and 86 are illustrated in the FIG. and encompass the geometrical sections 34 and 50 in the ramped or vaulted portions of the loop.

ALTERNATIVE EMBODIMENTS

Figure 4:
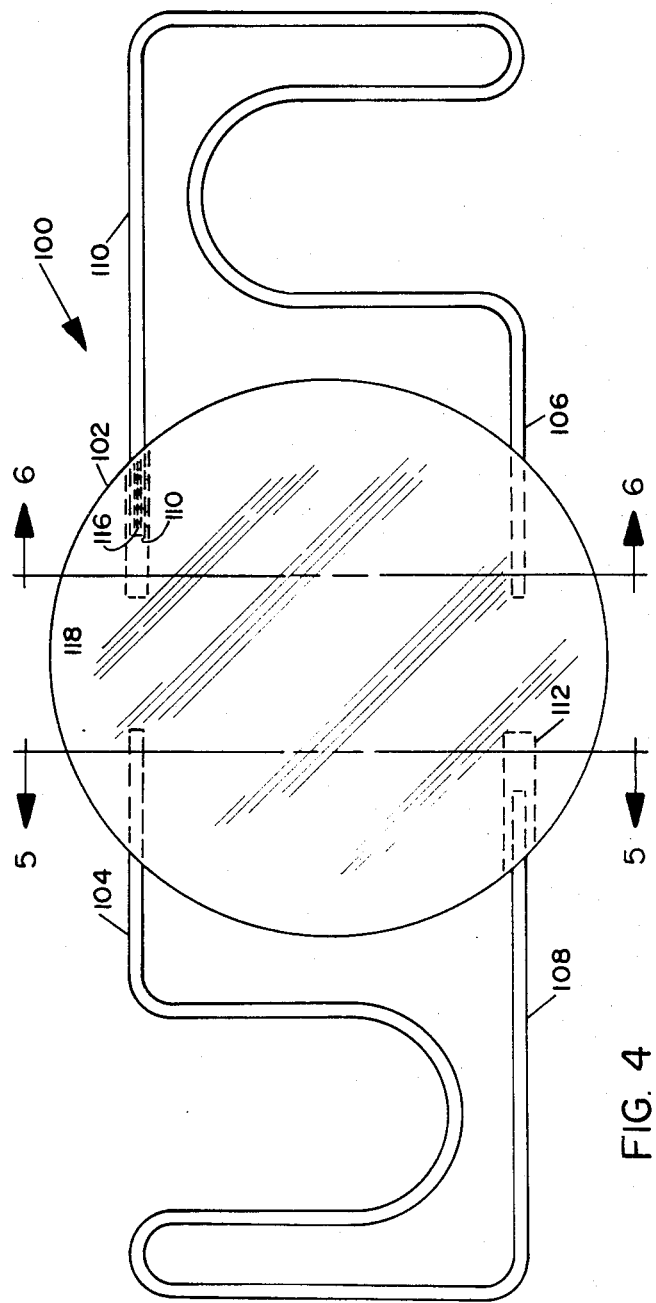
FIG. 4 illustrates another alternative embodiment of the all-size lens.

FIG. 4 illustrates an all-size lens 100 including planoconvex lens 102, flexible loops 104 and 106 and slidable ends 108 and 110 of the flexible loops. The principles of operation of the slidable ends are identical to those previously discussed. The significant aspects and features of the alternative embodiment are pressure-relief systems where the slidable end 108 is a first principle of different geometrical cross sections of the loop with respect to a hole 114, while the slidable end 110 is a second principle of a different predetermined geometrical cross section 116 in the hole 118, both of these principles now discussed with respect to the following two figures.

Figure 5:
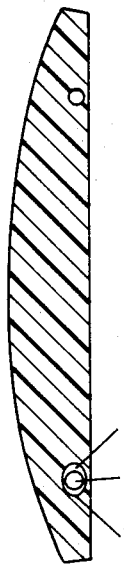
FIG. 5 illustrates a sectional view taken along line 5—5 of FIG. 4.

FIG. 5 illustrates a sectional view taken along line 5—5 of FIG. 4 illustrating the first principle of a cross section of the loop 108 and the cross section of the hole 112 which assumes a different and slightly larger cross-sectional area than the loop 108. The geometrical configuration is such that the cross-sectional dimensions of the hole would include an elongated circular configuration with dimensions which might be described as ovoid, paraboloid, elliptical, etc. The principle is to allow for a sliding engagement of the end of the loop 108 while providing for additional free area to permit air presssure and any fluid to flow in between the outer surface of the loop 108 and the inner surface of the hole 112 providing free space 114.

Figure 6:
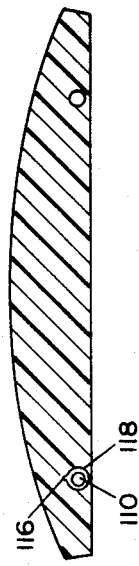
FIG. 6 illustrates a sectional view taken along line 6—6 of FIG. 4.

FIG. 6 illustrates a sectional view taken along line 6—6 of FIG. 5 illustrating the second principle of a circular cross section of the loop 110, the circular cross section of the hole 118 and a notch 116 provided in the hole 118. While the hole is illustrated as having a circular cross section with the notched groove 116, the hole could also have a non-circular cross section in addition to the notched groove 116. The notched groove 116 is illustrated by way of example and for purposes of illustration only and can assume any predetermined geometrical configuration such as a channel, trough or slight groove, and is not to be construed as limited to a notched V groove. Free space 120 is provided as a pressure-relief port.

ADDITIONAL ALTERNATIVE EMBODIMENTS

Figure 7:
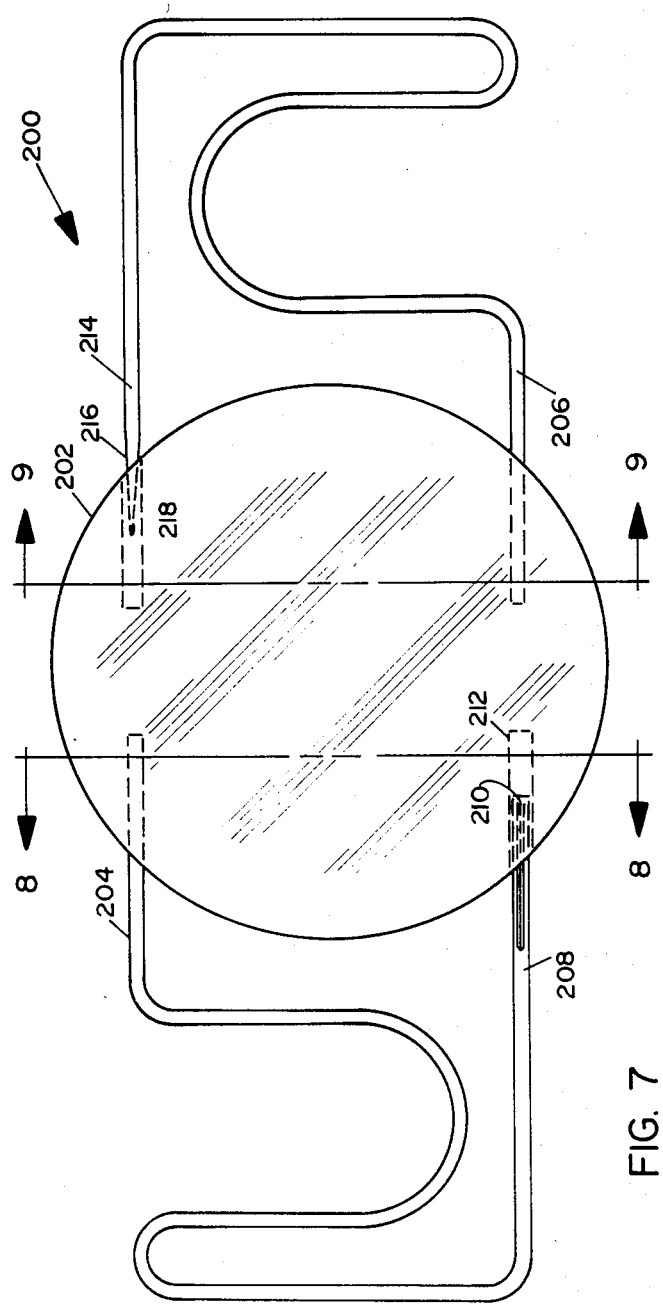
FIG. 7 illustrates an additional alternative embodiment of the all-size lens.

FIG. 7 illustrates a top view of an additional embodiment of an all-size lens 200. The all-size lens 200 includes a plano-convex lens 202, and flexible closed loops 204 and 206. The first principle of a slidable notched end 208 with V-notch 210 of the loop 204 and the second principle of a tapered end 214 of loop 206 are now described in detail providing free space as a pressure-relief port.

Figure 8:
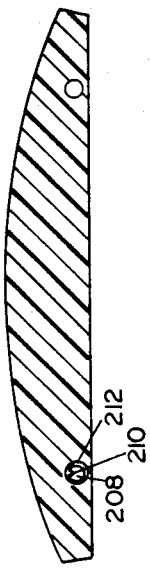
FIG. 8 illustrates a sectional view taken along line 8—8 of FIG. 7.

FIG. 8 illustrates a sectional view taken along line 8—8 of FIG. 7 illustrating the principle of a slidable end 208 including a V-notched groove 210 in the end of the flexible loop 204 in hole 212. This V-notched groove which can be any predetermined geometrical cross section such as ovoid, paraboloid, semi-circle, channel, etc. extends partially along the distance of the loop and provides for pressure relief. The hole 212 has a substantially circular cross section and is slightly larger in diameter than the diameter of the slidable end 208. The V-notched groove 210 provides that any fluid or air pressure can flow along this cross-sectional void out beyond the edge of the lens.

Figure 9:
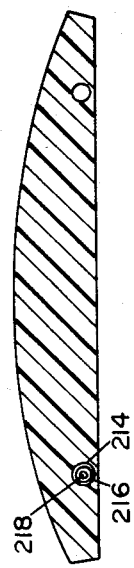
FIG. 9 illustrates a sectional view taken along line 9—9 of FIG. 7.

FIG. 9 illustrates a sectional view taken along line 9—9 of FIG. 7 illustrating the principle of a slidable end 214 of the loop 206 which is tapered about a length slightly beyond the edge of the lens as a decreasing taper 216. This taperedness provides for pressure relief. The taper is illustrated as coming to a blunt point 218 at the end, and tapering out to a geometrical cross section of the loop member about a finite length of the slidable end of the loop. The taper runs from point 220 to the end 218 and is a decreasing taper to the reduced diameter end 218.

MODE OF OPERATION

FIGS. 1 and 2 illustrate the slidable, adjustable and pressure-relieving aspects and features of the present invention. The sliding interaction between the end of the loops 26 and 40 within the holes 52 and 54 provides for slidable engagement and inherent adjustment of the size of the loops 18 and 20. The end of the loop slides within the depth of the hole due to interaction of the forces and pressures inherently in the eye when the base of the loop is pushed up against the interior chamber of the eye. This provides that the end of the loop will slide within the depth of the hole while adjusting to the interior of the eye. During the slidable engagement, additional adjustment and positioning of the loop is inherently adsorbed and taken up by the geometrical sections 34 and 50 which are illustrated as "U-shaped" curves, or more broadly, "S-shaped" curves or the like. These geometrical sections take up and adjust and expand as required while maintaining the arms of the loops in a substantially parallel position with respect to each other.

Finally, any pressure which may build up in the holes such as fluid or gas is easily eliminated through pressure ports 52 and 54 which can extend out through the plano surface, convex, or through the edge as is illustrated in the alternative embodiment of FIG. 3.

FIGS. 1 and 2 illustrate the principles of the slidable engagement of the ends of the loops, the adjustment of the mid portion of the loops, and the relieving of pressure at the ends of the loops. These principles of operation are applicable to any intraocular lens having loop members closed or open and are not limited to the specific embodiment of lens disclosed in FIGS. 1 and 2 or any of the other figures of this patent.

FIGS. 1 and 2 illustrate all three principles of the present invention of this patent; that is, the sliding of the free end, the adjustment over a portion of the loop structure with a geometrical section, and the relieving of any pressure which may build up at the free end of the lens.

FIG. 3 illustrates that the pressure-relief port can extend through the sides of the lens opposed to the plano or convex surfaces. The pressure-relief ports can be of a smaller diameter than the hole accommodating the slidable end of the loop or can be of a like or larger diameter as desired.

FIGS. 4–6 illustrate different embodiments where the hole is configured to provide inherent pressure relief. FIG. 5 illustrates that the hole can be of a different geometrical cross section than the cross section of the end of the loop, providing for passage of pressure between the free space provided therein. FIG. 6 illustrates that a channel of a geometrical cross section can be provided within the hole, providing additional free space for the passage and relief of pressure. The hole assumes a slightly larger cross section than the end of the loop.

FIGS. 7–9 illustrate that the slidable end of the loop can be provided with structure of geometrical sections for providing for passage of pressure. FIG. 8 illustrates that the slidable end of the loop can include an elongated groove or other elongated cross section providing for passage of pressure while FIG. 9 illustrates that the slidable end can have a taper of decreasing diameter thereby providing for slidable engagement as well as passage of pressure along the decreasing diameter. While the hole is a constant diameter, the cross section of the loop is either varying or assumes a different cross section than that of the hole.

Various modifications can be made to the present invention without departing from the apparent scope thereof. The principles of the present invention are applicable to any lens, either solely, jointly, or in combination with each other. The lens can be an anterior chamber lens or posterior chamber lens. While the invention of the geometrical section has been illustrated for closed loops, the same is applicable to an open loop.

Having thus described the invention, what is claimed is:

1. Intraocular lens for implant in an eye, said lens comprising:
   a. plano-convex lens including a plano surface, a convex surface, and a finite edge surface about a junction between said plano surface and said convex surface;
   b. plurality of closed loops for supporting said lens in said eye, said loops including two ends, one of said ends secured to said edge surface of said lens;
   c. hole means for slidable engagement positioned in said lens and supporting each other end of said loop, whereby each of said loops is inherently adjustable in the eye thereby providing an all-size lens; and,
   d. pressure relieving means in said lens between said hole means and at a substantially right angle to a surface of said lens.

2. Lens of claim 1 including means in said loop for adjusting size of said loops when said free end of said loop is in slidable engagement with said hole.

3. Lens of claim 2 wherein said adjusting means comprises a geometrical section of loop material positioned in at least one of said loops.

4. Lens of claim 3 wherein said adjusting means is an elongated U-shaped curve in one of said loops.

5. Lens of claim 4 wherein said curve is positioned in secured arm of said loop.

* * * * *